United States Patent
Paxton et al.

(10) Patent No.: US 8,594,972 B2
(45) Date of Patent: Nov. 26, 2013

(54) SYSTEM AND METHOD FOR TOMOGRAPHIC RETRIEVAL OF PARAMETER PROFILE FROM TRAVELING PATH

(75) Inventors: Larry J. Paxton, Laurel, MD (US);
Joseph M. Comberiate, Columbia, MD (US); Michael A. Kelly, Bristow, VA (US)

(73) Assignee: The Johns Hopkins University, Baltimore, MD (US)

(*) Notice: Subject to any disclaimer, the term of this patent is extended or adjusted under 35 U.S.C. 154(b) by 358 days.

(21) Appl. No.: 13/159,007

(22) Filed: Jun. 13, 2011

(65) Prior Publication Data
US 2012/0116713 A1    May 10, 2012

Related U.S. Application Data

(60) Provisional application No. 61/353,707, filed on Jun. 11, 2010.

(51) Int. Cl.
*G06F 15/00* (2006.01)

(52) U.S. Cl.
USPC .......... 702/150; 702/2; 702/3; 702/4; 702/15; 250/372; 250/283; 701/472; 348/36; 348/148; 348/222.1; 345/156

(58) Field of Classification Search
USPC .......... 702/2, 3, 4, 15; 250/372, 283; 348/36, 348/148, 222.1; 345/156
See application file for complete search history.

(56) References Cited

U.S. PATENT DOCUMENTS

| | | | |
|---|---|---|---|
| 6,167,347 A * | 12/2000 | Lin | 701/472 |
| 6,246,960 B1 * | 6/2001 | Lin | 701/472 |
| 6,697,736 B2 * | 2/2004 | Lin | 701/472 |
| 6,714,868 B2 * | 3/2004 | Picone et al. | 702/3 |
| 6,734,966 B2 | 5/2004 | McCarthy | |
| 6,809,818 B2 | 10/2004 | Hillis et al. | |
| 7,161,616 B1 * | 1/2007 | Okamoto et al. | 348/148 |
| 7,212,283 B2 | 5/2007 | Hother et | |
| 7,277,797 B1 * | 10/2007 | Kunitsyn et al. | 702/15 |
| 7,345,286 B2 * | 3/2008 | Picone | 250/372 |
| 2003/0149528 A1 * | 8/2003 | Lin | 701/214 |
| 2008/0177473 A1 | 7/2008 | Charbon et al. | |
| 2010/0063733 A1 | 3/2010 | Yunck | |
| 2010/0288910 A1 | 11/2010 | Robinson et al. | |
| 2011/0032357 A1 * | 2/2011 | Kitaura et al. | 348/148 |
| 2012/0140988 A1 * | 6/2012 | Takahashi | 382/103 |

FOREIGN PATENT DOCUMENTS

WO     02/18874     3/2002

\* cited by examiner

*Primary Examiner* — Carol S Tsai
(74) *Attorney, Agent, or Firm* — Noah J. Hayward

(57) ABSTRACT

A system for measuring a parameter of a medium with a vehicle moving in a traveling direction through the medium includes four detecting portions and a calculating portion. The four detecting portions respectively detect first through fourth values of the parameter from first through fourth lines-of-sight in first through fourth directions at first through fourth positions of the vehicle at first through fourth times. The first line-of-sight and the third line-of-sight are in a first plane and intersect at a first intersection, while the second line-of-sight and the fourth line-of-sight are in a second plane and intersect at a second intersection. The calculating portion calculates the parameter based on the first through fourth values and the first and second intersections.

18 Claims, 7 Drawing Sheets ns of the Earth's atmosphere.

SYSTEM AND METHOD FOR TOMOGRAPHIC RETRIEVAL OF PARAMETER PROFILE FROM TRAVELING PATH

CROSS REFERENCE TO RELATED APPLICATIONS

This application claims priority to U.S. provisional application Ser. No. 61/353,707, filed Jun. 11, 2010, the entire disclosure of which is incorporated herein by reference.

BACKGROUND OF THE INVENTION

1. Field of the Invention

The present invention relates to systems and methods for determining ionic or neutral concentrations within a medium using a passive remote sensing technique.

2. Description of the Related Art

FIG. 1 illustrates different atmospheric layers of the Earth's atmosphere.

As shown in the figure, up to about 14 kilometers (km) directly above the Earth 100 is the troposphere 102. After the troposphere 102 is the tropopause 104, which is only about 4 km thick. The stratosphere 106 is directly above the tropopause 104. Within the stratosphere 106 is the ozone layer 108. Next is the mesosphere 110, which is about 40 km thick. Finally, the ionosphere 112, directly above the mesosphere 110, is hundreds of kilometers thick. The neutral component of the atmosphere above the mesosphere is referred to as the thermosphere. Together, the ionosphere, thermosphere and mesosphere are commonly referred to as the upper atmosphere.

With respect to telecommunications, the ionosphere is particularly important.

The ionosphere is the ionized part of the atmosphere produced primarily by the absorption of solar radiation. The principle component of the upper part of the ionosphere is singly ionized atomic oxygen (O+). The ionosphere has practical importance because, among other functions, it influences radio wave propagation to distant places on the Earth. The influence extends across a wide range of radio frequency bands, well above the high frequency band, considered to be 3-30 megahertz (MHz.) The effects include impacts on radio transmissions in all bands, e.g., amplitude modulation (AM), frequency modulation (FM), shortwave, etc., and radars (including over the horizon radars).

Satellite-borne remote sensing of the ionosphere observe emissions by atomic ions (singly ionized atomic oxygen (O+)) and the neutral components of the upper atmosphere such as atomic oxygen (O), molecular oxygen ($O_2$), molecular nitrogen ($N_2$), nitric oxide (NO), ozone ($O_3$), helium (He), hydrogen (H). FIGS. 2A-2C illustrate such a system.

FIGS. 2A-C illustrate a conventional satellite-based method of measuring ionic concentrations within the Earth's ionosphere. FIG. 2A illustrates measurements taken at a first time $t_1$. FIG. 2B illustrate measurements taken at a second time $t_2$. FIG. 2C illustrate locations of calculated ionic concentrations using the measurements at times $t_1$ and $t_2$.

As shown in FIG. 2A, a satellite 202 and a satellite 204 are located in space 206 above the Earth's ionosphere 208, which is illustrated as having a lower boundary 210 and an upper boundary 212.

At time $t_1$, satellite 202 measures the total emissions of a particular ion along a line-of-sight (LOS) 214, whereas satellite 204 measures the total emissions of the ion along a LOS 216, a LOS 218 and a LOS 220.

In the conventional method of FIG. 2A, satellite 202 is able to detect a total of emissions by a particular ion, for example, atomic oxygen ions ($O^+$), within ionosphere 208 along LOS 214.

What is more valuable for radio wave communications is an altitude profile of the amount of the particular ion, in this example atomic oxygen ions ($O^+$) at each altitude z, or [$O^+$](z). In other words, in addition to the total amount of emission along LOS 214, an altitude function [$O^+$](z) of the $O^+$ number density along LOS 214 would be valuable. A mapping of such altitude functions along the path of a vehicle traveling above the earth would greatly enable high frequency (HF) communication systems to compensate for negative impacts of our otherwise imperfect knowledge of the altitude profile of atomic oxygen ions on HF and radio frequency signals.

The altitude function of the particular ion is formulated by tomographic retrieval. The mathematical basis for tomographic retrieval is applied to obtain cross-sectional images and is based on the notion that a projection of an object at a given angle θ is made up of a set of line integrals. In ionospheric observations, the line integral represents the total emissions along a line-of-sight (LOS) through the ionosphere. It is known that if there are an infinite number of one-dimensional projections of an object taken at an infinite number of angles, the original object can be reconstructed. To accomplish this, a filtered back projection algorithm is used. Accordingly, to find the altitude function of the particular ion, the individual ion concentrations along LOS 214 via satellite 204 are first determined. For example, satellite 204 is able to detect a total of emissions by the same ion as satellite 202, in this example $O^+$, within ionosphere 208 along LOSs 216, 218 and 220.

Here, LOSs 214, 216, 218 and 220 are in the same plane, i.e. the plane of the figure, such that: LOS 214 intersects with LOS 216 at location 222; LOS 214 intersects with LOS 218 at location 224; and LOS 214 intersects with LOS 220 at location 226. Clearly, satellite 204 may detect total emissions within ionosphere 208 along more LOSs, however, for purposes of discussion, a sampling of LOSs 216, 218 and 220 are provided.

In order to tomographically retrieve the ion altitude function of the entire plane of ionosphere 208 (a ribbon in the plane of the figure), satellites 202 and 204 must scan additional areas. This will be described with reference to FIG. 2B.

As shown in FIG. 2B, satellite 202 and satellite 204 are located at new locations in space 206 above ionosphere 208.

At time $t_2$, satellite 202 measures the total emissions of the particular ion along a LOS 228, whereas satellite 204 measures the total emissions of the ion along a LOS 230, a LOS 232 and a LOS 234.

Here, LOSs 228, 230, 232 and 234 are in the same plane, i.e. the plane of the figure, such that: LOS 228 intersects with LOS 230 at location 236; LOS 228 intersects with LOS 232 at location 238; and LOS 228 intersects with LOS 234 at location 240. Clearly, satellite 204 may detect total emissions within ionosphere 208 along more LOSs, however, for purposes of discussion, a sampling of LOSs 230, 232 and 234 are provided.

The detected total emissions along a LOS includes emission contributions from ions within the LOS in addition to emission contributions from neighboring ions, taking into account secondary emission issues related to resonance, fluorescence, etc. This will be described with reference to FIG. 2C.

As shown in FIG. 2C, locations 222, 224 and 226 are determined from the intersecting LOSs of FIG. 2A, whereas locations 236, 238 and 240 are determined from the intersecting LOSs of FIG. 2B. Here the emission detected by satellite 202 (and 204 for that matter) at location 222 includes secondary emissions related to resonance, fluorescence, etc., as contributed by the ions at locations 224, 226, 236, 238 and 240. Similarly, emission detected by satellite 202 (and 204 for that matter) at location 236 includes secondary emissions related to resonance, fluorescence, etc., as contributed by the ions at locations 222, 224, 226, 238 and 240.

As satellites 202 and 204 scan the remainder of the plane within ionosphere 208, an array of emission values will be determined. If more LOSs are used, then more emission values will be determined, i.e., the larger the array. Once the emission values are determined, any known method may be used to determine the ion altitude function for the entire plane of ionosphere 208.

Once the ion altitude function for the entire plane of ionosphere 208 is known, it may be taken into account when transmitting/receiving signals therethrough.

All conventional systems for measuring ionic concentrations within the Earth's ionosphere are not satellite-based.

FIGS. 3A-C illustrate a conventional system of ground-based detectors used to deduce the properties of the ionosphere. The geometry illustrated in FIG. 3A-C has been applied to radio-based remote sensing of ionospheric properties. FIG. 3A illustrates measurements taken at a first time $t_1$. FIG. 3B illustrate measurements taken at a second time $t_2$. FIG. 3C illustrates locations of calculated ionic concentrations using the measurements at times $t_1$ and $t_2$.

As shown in FIG. 3A, a ground-based detector 302 and a ground-based detector 304 are located below ionosphere 208. The system of FIG. 3A operates in a similar manner to that of the system of FIG. 2A. However, in the system of FIG. 3A, the LOSs are directed from the Earth to ionosphere 208.

At time $t_1$, ground-based detector 302 measures the total emissions of a particular ion along a LOS 314, whereas ground-based detector 304 measures the total emissions of the ion along a LOS 316, a LOS 318 and a LOS 320.

The altitude function of the particular ion is formulated by initially finding individual ion concentrations along LOS 314 via ground-based detector 302. Ground-based detector 304 is able to detect a total of emissions by the same ion ground-based detector 302, in this example $O^+$, within ionosphere 208 along LOSs 316, 318 and 320.

Here, LOSs 314, 316, 318 and 320 are in the same plane, i.e. the plane of the figure, such that: LOS 314 intersects with LOS 316 at location 322; LOS 314 intersects with LOS 318 at location 324; and LOS 314 intersects with LOS 320 at location 326. Clearly, ground-based detector 304 may detect total emissions within ionosphere 208 along more LOSs, however, for purposes of discussion, a sampling of LOSs 316, 318 and 320 are provided.

As shown in FIG. 3B, ground-based detector 302 and ground-based detector 304 are located in the same positions as described above with reference to FIG. 3A. However, in this situation, ground-based detector 302 is detecting along a new LOS and ground-based detector 304 is detecting along new LOSs.

At time $t_2$, ground-based detector 302 measures the total emissions of the particular ion along a LOS 328, whereas ground-based detector 304 measures the total emissions of the ion along LOS 330, a LOS 332 and a LOS 334.

Here, LOSs 328, 330, 332 and 334 are in the same plane, i.e. the plane of the figure, such that: LOS 328 intersects with LOS 330 at location 336; LOS 328 intersects with LOS 332 at location 338; and LOS 328 intersects with LOS 334 at location 340. Clearly, ground-based detector 304 may detect total emissions within ionosphere 208 along more LOSs, however, for purposes of discussion, a sampling of LOSs 330, 332 and 334 are provided.

As mentioned previously, the detected total emission along a LOS includes emission contributions from ions within the LOS in addition to emission contributions from neighboring ions, taking into account secondary emission issues related to resonance, fluorescence, etc. This will be further described with reference to FIG. 3C.

As shown in FIG. 3C, locations 322, 324 and 326 are determined from the intersecting LOSs of FIG. 3A, whereas locations 336, 338 and 340 are determined from the intersecting LOSs of FIG. 3B. Here the emission detected by ground-based detector 302 (and 304 for that matter) at location 322 includes secondary emissions related to resonance, fluorescence, etc., as contributed by the ions at location 324, 326, 336, 338 and 340. Similarly, emission detected by ground-based detector 302 (and 304 for that matter) at location 336 includes secondary emissions related to resonance, fluorescence, etc., as contributed by the ions at location 322, 324, 326, 338 and 340.

As ground-based detectors 302 and 304 scan the remainder of the plane within ionosphere 208, an array of emission values will be determined. If more LOSs are used, then more emission values will be determined, i.e., the larger the array. Once the emission values are determined, any known method may be used to determine the ion altitude function for the entire plane of ionosphere 208.

Once the ion altitude function for the entire plane of ionosphere 208 is known, it may be taken into account when transmitting/receiving signals therethrough.

Of the conventional systems discussed above, they are limited to determining the ion altitude function from above a medium or from below a medium.

What is needed is system and method for determining the ion altitude function of a medium from within the medium.

SUMMARY OF THE INVENTION

The present invention provides a system and method for determining the ion altitude function of a medium from within the medium.

In accordance with aspects of the present invention, a system measures a parameter of a medium with a vehicle moving in a traveling direction through the medium. The system includes four detecting portions and a calculating portion. The first detecting portion detects a first value of the parameter from a first line-of-sight in a first direction at a first position of the vehicle at a first time. The second detecting portion detects a second value of the parameter from a second line-of-sight in a second direction at a second position of the vehicle at a second time. The third detecting portion detects a third value of the parameter from a third line-of-sight in a third direction at a third position of the vehicle at a third time. The fourth detecting portion detects a fourth value of the parameter from a fourth line-of-sight in a fourth direction at a fourth position of the vehicle at a fourth time. The calculating portion calculates the parameter based on the first value, the second value, the third value, and the fourth value. The first line-of-sight and the third line-of-sight are in a first plane and intersect at a first intersection. The second line-of-sight and the fourth line-of-sight are in a second plane and intersect at a second intersection. The calculating portion calculates the parameter based, additionally, on the first intersection and the second intersection.

Additional advantages and novel features of the present invention are set forth in the various embodiments described in more detail in the description which follows, and will become more readily apparent to those of ordinary skill in the art upon examination of the following, or may be learned by practice of the invention. The numerous advantages of the invention are realized and attained by the instrumentalities and combinations particularly pointed out in the appended claims. It will be understood that the embodiments described herein are exemplary, and thus do not restrict the scope of the invention.

BRIEF SUMMARY OF THE DRAWINGS

The accompanying drawings, which are incorporated in and form a part of the specification, illustrate exemplary embodiments of the present invention and, together with the description, explain, but do not restrict, the present invention. In the drawings:

FIG. 2A illustrates measurements taken at a first time $t_1$; FIG. 2B illustrate measurements taken at a second time $t_2$; and FIG. 2C illustrate locations of calculated ionic concentrations using the measurements at times $t_1$ and $t_2$;

FIG. 3A illustrates measurements taken at a first time $t_1$; FIG. 3B illustrate measurements taken at a second time $t_2$; and FIG. 3C illustrate locations of calculated ionic concentrations using the measurements at times $t_1$ and $t_2$;

FIG. 4A illustrates measurements taken at a first time $t_1$; FIG. 4B illustrates measurements taken at a second time $t_2$; and FIG. 4C illustrates locations of calculated ionic concentrations using the measurements at times $t_1$ and $t_2$;

DETAILED DESCRIPTION

In accordance with exemplary embodiments of the present invention, a sensor design permits imaging of structures in a layer of the atmosphere from a vehicle traveling within the layer of the atmosphere. An example embodiment uses a hyperspectral imager that scans from near zenith to below the local horizon to image the atmosphere in predetermined wavelengths. The spectral signatures imaged contain information about the line-of-sight (LOS) density of the neutral and ionized constituents. These spectral signatures, when combined with the viewing geometry, enable retrieval of the ion altitude function of the layer of the atmosphere. These data can be used to evaluate the electron density profiles (EDP) and scintillation profiles that impact space operations.

In an example embodiment, a spectrograph is used as a sensor that operates in the ultraviolet range from about 40 nanometers (nm) to 300 nm. This spectral region contains the signatures of the major species in the upper atmosphere (also known as the thermosphere) and the ionosphere. In particular, atomic oxygen (O), molecular oxygen ($O_2$), molecular nitrogen ($N_2$), nitric oxide (NO), ozone ($O_3$), helium (He), hydrogen (H) and singly ionized atomic oxygen (O+) can be observed. From these species, electron density profiles can be retrieved. The sensor includes an imaging spectrograph (e.g., a spectrograph with the capability of producing spatial information along the slit direction) coupled to a mirror that scans the field of regard of the instrument. The field of regard is scanned in the vertical plane.

The system design and operation produces a two-dimensional set of intersecting lines-of-site (LOSs). This set of intersecting LOSs specifies the two dimensional structure of the emitting layer. This technique works when the sensor is immersed in the radiating medium, for example. If the system is above the radiating layer the field of regard of the sensor may be changed in order to achieve a sampling density sufficient to uniquely specify the emitting region. Multispectral imagery may be used in order to be able to accurately account for other emission mechanisms.

An example system and method for calculating ionic concentrations within the Earth's ionosphere, in accordance with aspects of the present invention will now be described in further detail with reference to FIGS. 4A-7.

Figure 4A:
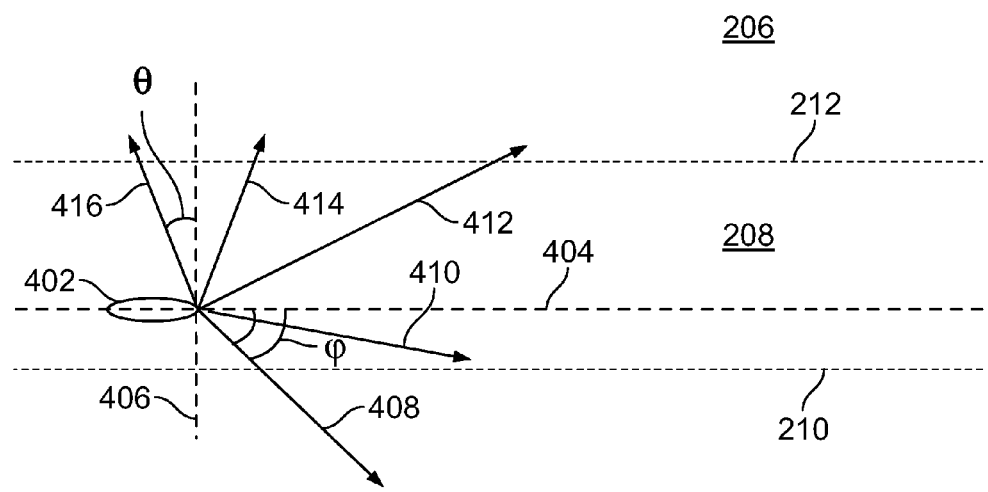
FIGS. 4A-C illustrate a system and method of measuring ionic concentrations within the Earth's ionosphere in accordance with the present invention.
Figure 4B:
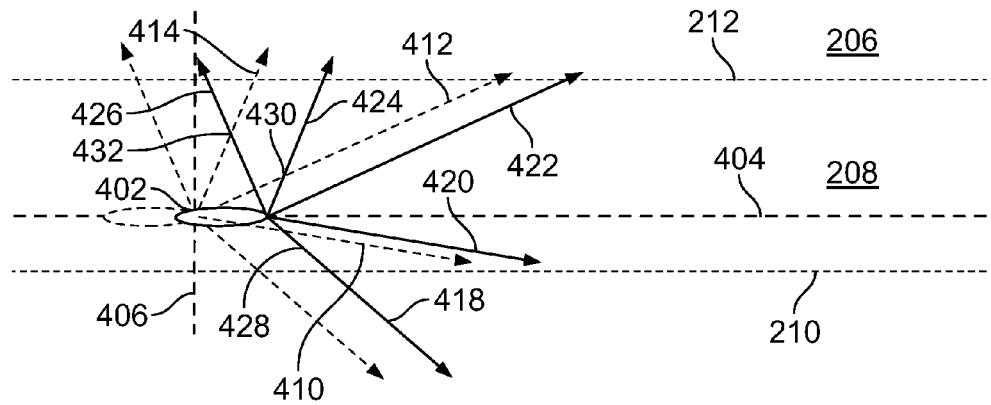
Figure 4C:
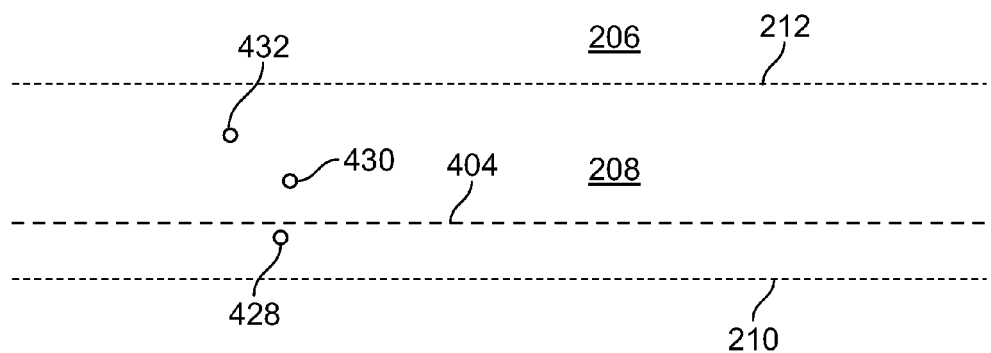

FIGS. 4A-C illustrate a system and method of measuring ionic concentrations within the Earth's ionosphere in accordance with one or more exemplary embodiments of the present invention. FIG. 4A illustrates measurements taken at a first time $t_1$. FIG. 4B illustrates measurements taken at a second time $t_2$. FIG. 4C illustrates locations of calculated ionic concentrations using the measurements at times $t_1$ and $t_2$.

As shown in FIG. 4A, a detecting vehicle 402 is traveling through ionosphere 208, along a path indicated by dotted line 404. A zenith direction indicated by the dotted line 406 is normal to the traveling path, i.e., dotted line 406 is perpendicular to dotted line 404.

At time $t_1$, detecting vehicle 402 is operable to measure the total emissions of a particular ion along a LOS 408, a LOS 410, a LOS 412, a LOS 414 and a LOS 216. LOS 408 and LOS 410 are below the traveling direction. LOS 408, in particular is below the traveling direction by an angle φ, i.e., LOS 408 is below dotted line 404 by angle φ. LOS 416 is beyond the zenith direction by an angle θ, i.e., LOS 416 is beyond dotted line 406 by angle θ.

The scan range of detecting vehicle 402 is below detecting vehicle 402 and above detecting vehicle 402.

The altitude function of the particular ion is formulated by initially finding individual ion concentrations along a "fan" of LOSs 408, 410, 412, 414 and 416 via detecting vehicle 402. Another fan of LOSs will then be used, as will be described with reference to FIG. 4B.

As shown in FIG. 4B, detecting vehicle 402 is located at a new position along the path indicated by dotted line 404.

At time $t_2$, detecting vehicle 402 is operable to measure the total emissions of the particular ion along a LOS 418, a LOS 420, a LOS 422, a LOS 424 and a LOS 426. LOS 418 and LOS 420 are below the traveling direction. In particular, LOS 418 is below the traveling direction by angle φ, i.e., LOS 418 is below dotted line 404 by angle φ. LOS 426 is beyond the zenith direction by angle θ, i.e., LOS 426 is beyond dotted line 406 by angle θ.

Here, LOSs 408, 410, 412, 414 and 416 of FIG. 4A are in the same plane, i.e. the plane of the figure, and LOSs 418, 420, 422, 424 and 426 of FIG. 4B are in the same plane such that: LOS 410 intersects with LOS 418 at location 428; LOS 412 intersects with LOS 424 at location 430; and LOS 414 intersects with LOS 426 at location 432. Clearly, detecting vehicle 402 may detect total emissions within ionosphere 208 along more LOSs, however, for purposes of discussion, a sampling of LOSs is provided.

The detecting instrument on detecting vehicle 402 scans as detecting vehicle 402 moves along the path indicated by dotted line 404. Successive scans overlap. The multiple-overlapping LOSs provide the input to a tomographic retrieval of the ion altitude function above and below detecting vehicle 402, i.e., for the entire plane of ionosphere 208.

In order to map the ion altitude function for the entire plane of ionosphere 208, i.e., a ribbon in the plane of the figure, detecting vehicle 402 must scan additional areas.

As described previously, the detected total emission along a LOS includes emission contributions from ions within the LOS in addition to emission contributions from neighboring ions, taking into account secondary emission issues related to resonance, fluorescence, etc. This will be further described with reference to FIG. 4C.

Figure 1:
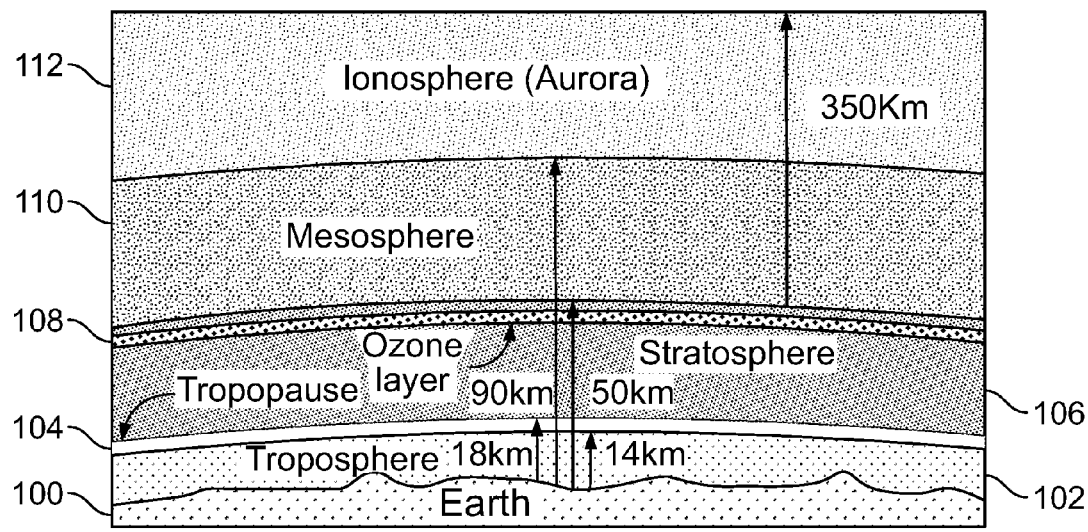
FIG. 1 illustrates the different atmospheric layers of the Earth's atmosphere.
Figure 2A:
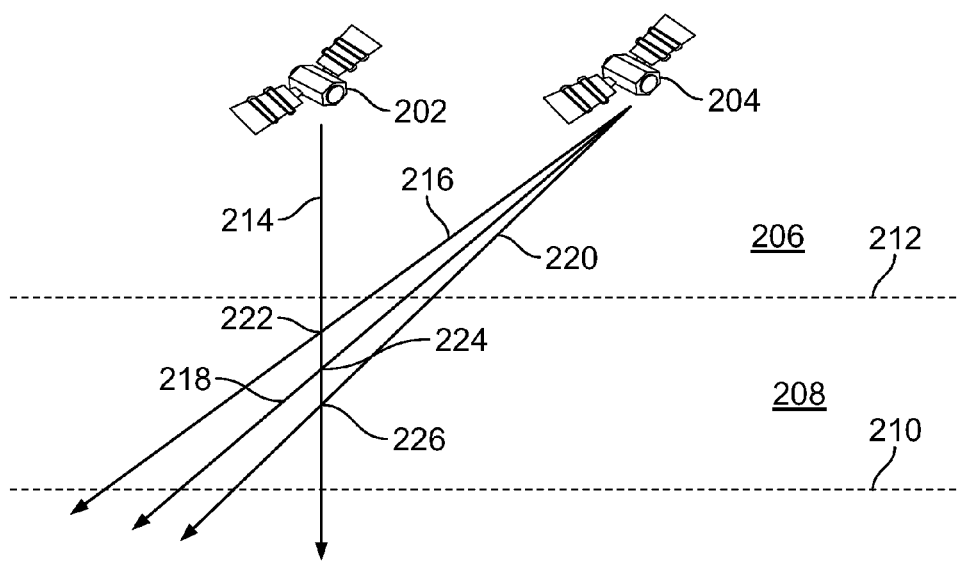
FIGS. 2A-C illustrate a conventional satellite-based method of measuring ionic concentrations within the Earth's ionosphere.
Figure 2B:
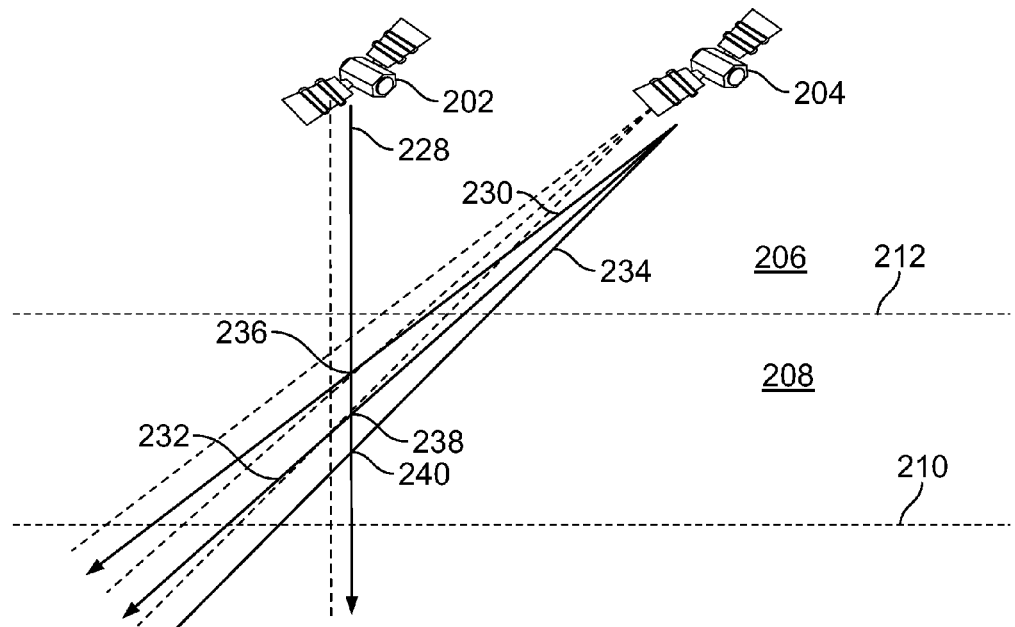
Figure 2C:
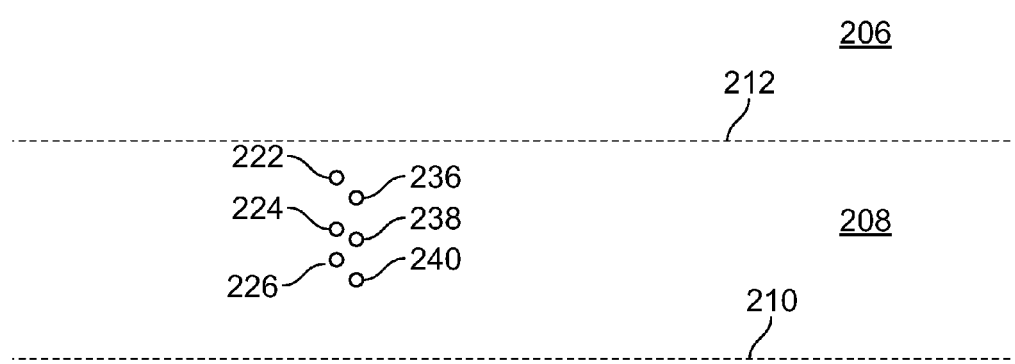

As shown in FIG. 4C, locations 432, 430 and 428 are determined from the intersecting LOSs of FIG. 4B. Here the emission detected by detecting vehicle 402 includes secondary emissions related to resonance, fluorescence, etc., as contributed by the ions at other locations as discussed above, for example with reference to FIGS. 2C and 3C.

As detecting vehicle 402 scans the remainder of the plane within ionosphere 208, an array of emission values will be determined. If more LOSs are used, then more emission values will be determined, i.e., the larger the array. Once the emission values are determined, any known method may be used to determine the ion altitude function for the entire plane of ionosphere 208. This will now be described with reference to FIG. 5.

Figure 5:
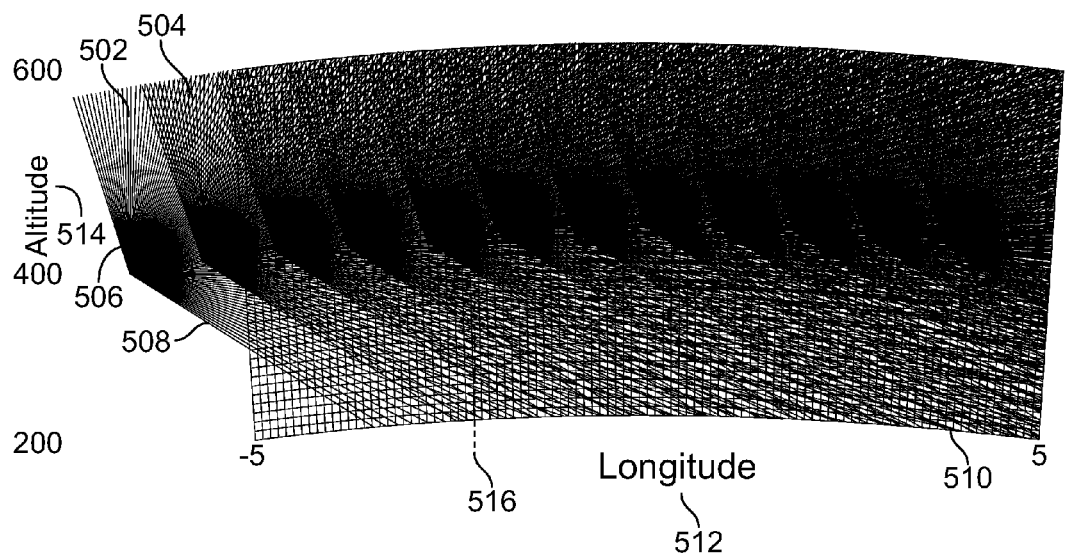
FIG. 5 illustrates an example resulting grid of calculated ionic concentrations within the Earth's ionosphere in accordance with the present invention.

FIG. 5 illustrates an example resulting grid of calculated ionic concentrations within the Earth's ionosphere in accordance with aspects of the present invention.

As shown in the figure, a detector is operable to detect along a plurality of "fans" of LOSs, a sampling of which is indicated as fan 502 and fan 504. Fan 502 spreads from a first LOS 506 through an oblique angle to an LOS 508. A grid 510 represents intersections of LOSs from the plurality of fans of LOSs. Grid 510, in this illustrative case, spans a longitude of 10° along an x-axis 512 and spans an altitude from 200 Km to 600 Km along a y-axis 514. An example sampling of ionic concentrations is shown by dotted line 516.

Once the ion altitude function for the entire plane of ionosphere 208 is known, it may be taken into account when transmitting/receiving signals therethrough.

Figure 6:
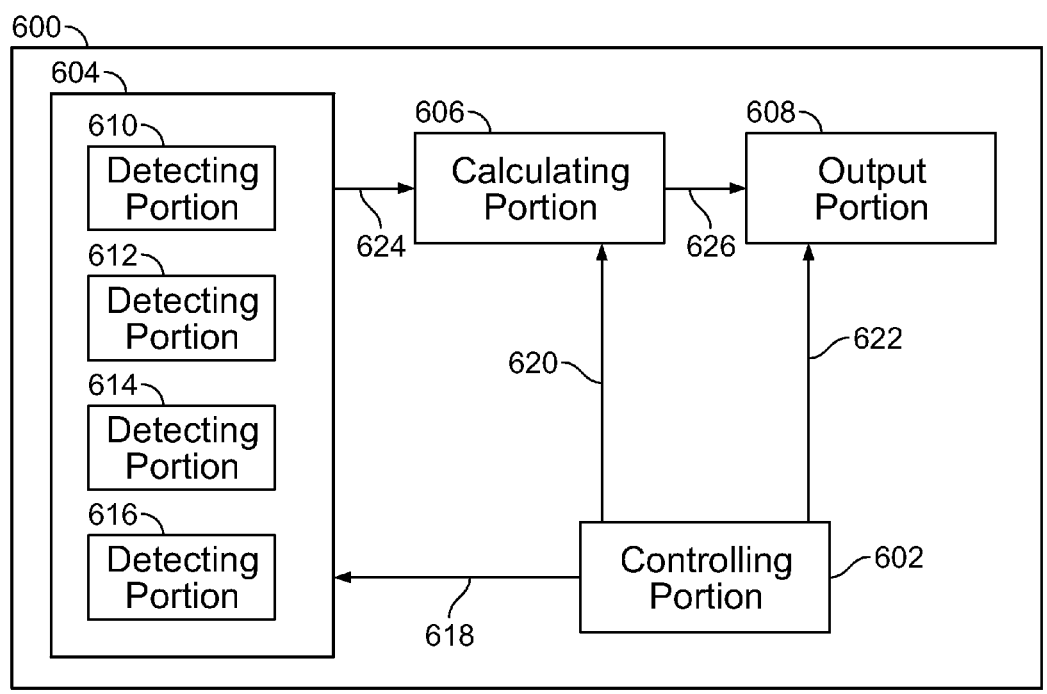
FIG. 6 illustrates an example system for calculating ionic concentrations within the Earth's ionosphere, in accordance with the present invention.

FIG. 6 illustrates an example system 600 for calculating ionic concentrations within the Earth's ionosphere, in accordance with aspects of the present invention.

As shown in the figure, system 600 includes a controlling portion 602, a detector 604, a calculating portion 606 and an output portion 608. Controlling portion 602, detector 604, calculating portion 606 and output portion 608 are illustrated as individual devices. However, in some embodiments, at least two of controlling portion 602, detector 604, calculating portion 606 and output portion 608 may be combined as a unitary device. Further, in some embodiments, at least one of controlling portion 602, detector 604, calculating portion 606 and output portion 608 may be implemented as a tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of tangible computer-readable media.

Detector 604 includes a detecting portion 610, a detecting portion 612, a detecting portion 614 and a detecting portion 616. Detecting portion 610, detecting portion 612, detecting portion 614 and detecting portion 616 are illustrated as individual devices. However, in some embodiments, at least two of detecting portion 610, detecting portion 612, detecting portion 614 and detecting portion 616 may be combined as a unitary device. Further, in some embodiments, at least one of detecting portion 610, detecting portion 612, detecting portion 614 and detecting portion 616 may be implemented as a tangible computer-readable media for carrying or having computer-executable instructions or data structures stored thereon.

Controlling portion is arranged to provide control signals 618, 620 and 622. Detector 604 is arranged to receive control signal 618 and output detected signal 624. Calculating portion 606 is arranged to receive control signal 620 and signal 624 and to output a calculated signal 626. Output portion 608 is arranged to receive control signal 622 and signal 626.

Operation of 600 will now be described with additional reference to FIG. 7.

Figure 7:
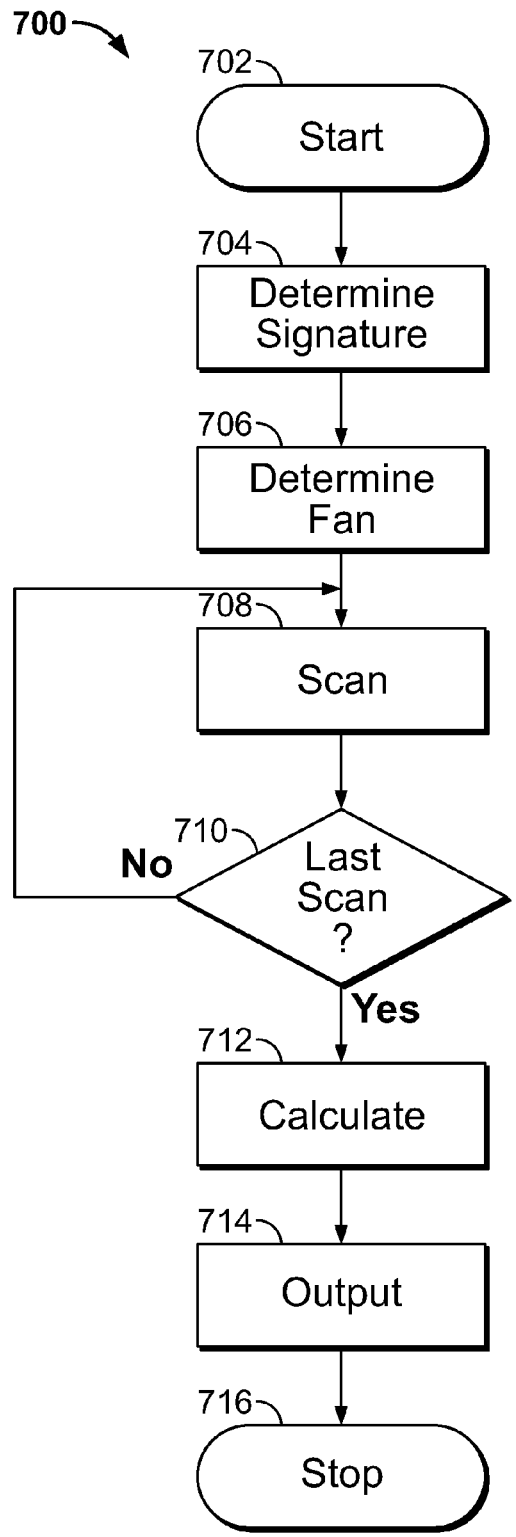
FIG. 7 illustrates an example method for calculating ionic concentrations within the Earth's ionosphere, in accordance with the present invention.

FIG. 7 illustrates an example method 700 for calculating ionic concentrations within the Earth's ionosphere, in accordance with aspects of the present invention.

Method 700 starts (S702) and the signatures for detection are determined (S704).

In an example embodiment, the emission signature for atomic oxygen (O) is selected. For example, detecting portion 610 may be operable to detect the signature of atomic oxygen. However, in other embodiments, the emission signature for molecular oxygen ($O_2$), molecular nitrogen ($N_2$), nitric oxide (NO), ozone ($O_3$), helium (He), hydrogen (H) and singly ionized atomic oxygen (O+) may be selected. For example, detecting portion 610 may be a hyperspectral imaging device operable to detect the signature of at least one of the group of molecular oxygen ($O_2$), molecular nitrogen ($N_2$), nitric oxide (NO), ozone ($O_3$), helium (He), hydrogen (H) and singly ionized atomic oxygen (O+). In such a case, controlling portion 602 may instruct detecting portion 610 as to which signatures it should detect. Still further, in the event that another medium is to be scanned, other emission signatures may be selected. In particular, scanning of the ionosphere is described herein as a non-limiting example—merely for purposes of explanation. Any medium, non-limiting examples of which include other layers of the atmosphere, or fluids such as oceans, may be scanned for predetermined emission signatures which for the purposes of explanation have been described as "light" or "optical emissions" herein but may consist of acoustic or other forms of energy.

The examples discussed above additionally include a single signature as a non-limiting example—merely for purposes of explanation. In other embodiments, a plurality of signatures may be detected, e.g., a hyperspectral scanning. This is described in greater detail below.

Once the signature is determined, then the scanning fan is determined (S706). For example, returning to FIG. 4A, the scanning fan includes five LOSs—LOS 408, LOS 410, LOS 412, LOS 414 and LOS 416. However, as seen in FIG. 5, the scanning fan includes many more LOSs, for example as seen in fan 502.

As the number of LOSs in a fan increases, required data processing resources increase. However, as the number of LOSs in a fan increases, the spacing between LOS intersections decreases, which ultimately provides a more precise ion altitude function.

With respect to the maximum scanning angle of the scanning fan, it may be of any angle. Returning to FIG. 4A, in example embodiments, the scanning fan should include an angle above the path indicated by dotted line 404, for example any one of LOS 412, LOS 414 and LOS 416. In the example of FIG. 4A, the maximum scanning angle is from LOS 408 to LOS 416 (including angles φ and θ). The scanning fan should additionally include an angle below the traveling direction indicated by dotted line 404, for example any one of LOS 410 and LOS 408. Geometrically speaking, including an angle above the direction of travel and including an angle below the direction of travel will ensure scanning of the entire medium in which detecting vehicle 402 is traveling.

Figure 3A:
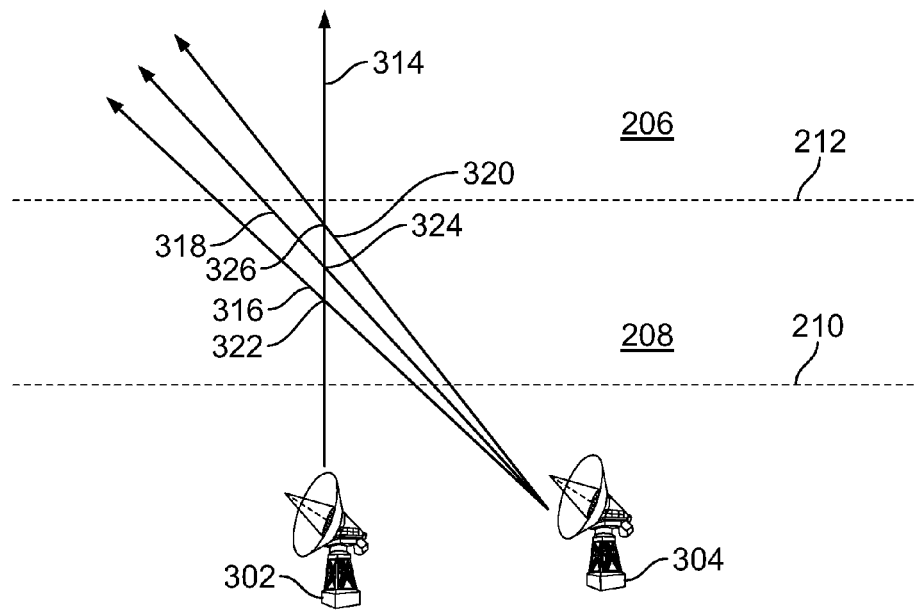
FIGS. 3A-C illustrate a conventional system of ground-based detectors used to deduce the properties of the ionosphere.
Figure 3B:
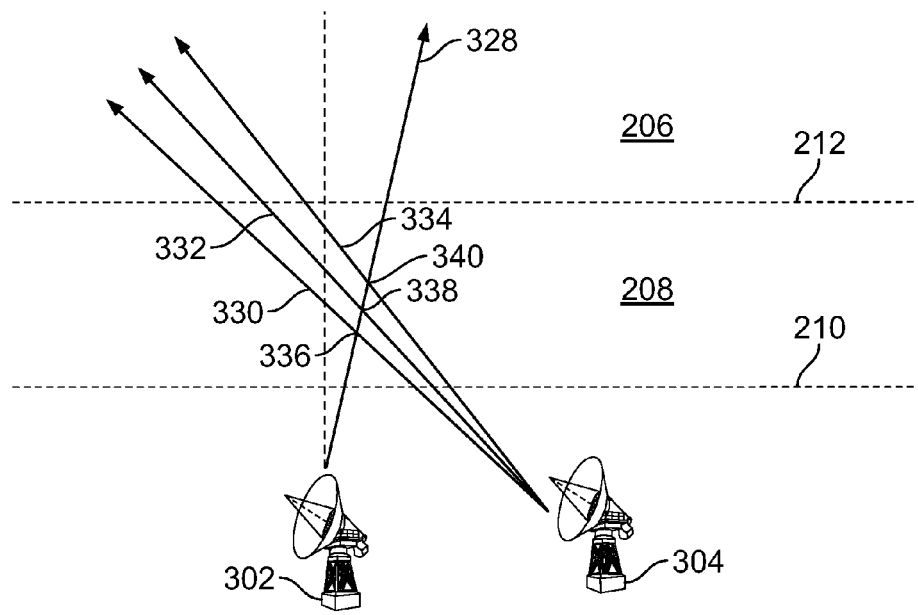
Figure 3C:
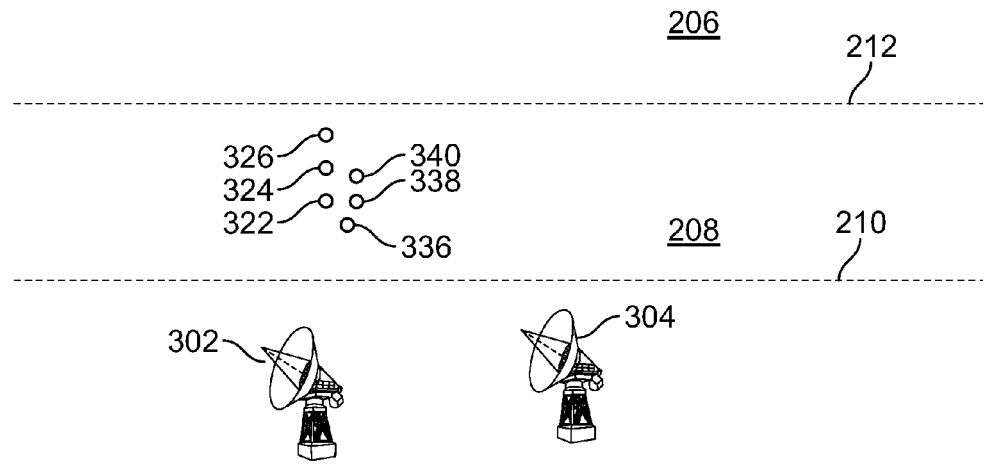

In an example embodiment, if the upper bound of the scanning fan is beyond the zenith direction (dotted line 406), this ensures adequate sampling of the medium above the detector. FIG. 3 illustrates this principle in action for the case of stationary ground sensors—lines of sight 330, 332, and 334 can, for the purposes of illustration, be thought of as the LOS past the vertical. The measurements from ground-based position 302 defining LOS 328 (which is not past vertical), when combined with those measurements from position 304, define points 336, 338 and 340. The exact range beyond the vertical is determined by the vertical resolution requirements of the measurements.

Returning to FIG. 6, controlling portion 602 may set maximum scan angle of the scanning fan. In some embodiments, the maximum scan angle may be predetermined and programmed within controlling portion 602. In other embodiments, the maximum scan angle may be remotely entered into controlling portion 602.

Controlling portion 602 may additionally set the number of LOSs. For example, as shown in FIG. 4A, controlling portion 602 would have set the number of LOSs to five, whereas as shown in FIG. 5, controlling portion 602 would have set the number of LOSs to a much larger number. In some embodiments, the number of LOSs may be predetermined and programmed within controlling portion 602. In other embodiments, the number of LOSs may be remotely entered into controlling portion 602.

Controlling portion 602 instructs detector 604 to scan via control signal 618. Detector 604 may be any known detecting system for detecting a desired parameter. In example embodiments, detector 604 is operable to detect emissions by atomic ions such as atomic oxygen (O), molecular oxygen ($O_2$), molecular nitrogen ($N_2$), nitric oxide (NO), ozone ($O_3$), helium (He), hydrogen (H) and singly ionized atomic oxygen (O+). Further, in some embodiments, detector 604 may be a hyperspectral detector operable to detect emission by atomic ions of any combination of the group of atomic oxygen (O), molecular oxygen ($O_2$), molecular nitrogen ($N_2$), nitric oxide (NO), ozone ($O_3$), helium (He), hydrogen (H) and singly ionized atomic oxygen (O+).

Detector 604 may scan by any known beam steering system and method. Non-limiting examples of beam steering systems and methods include electrical and mechanical beam steering systems and methods.

Returning to FIG. 7, once the scanning fan is determined, the medium is scanned (S708). For example, as shown in FIG. 4A, detecting vehicle detects an intensity value from LOS 408. This may be accomplished, as shown in FIG. 6, by detecting portion 610. Detector 604 knows where to start its scanning fan as instructed by controlling portion 602 via control signal 618. Accordingly, detecting portion 610 is directed to detect an intensity value along LOS 408. Detecting portion 610 may be any known type of intensity detector, a non-limiting example of which includes a photodiode. As mentioned previously, in some embodiments, detecting portion 610 may be a one or two dimensional array detector able to detect wavelength dependent intensity measurements over a wavelength range simultaneously. A system operable to detect an intensity value corresponding to a plurality of distinct wavelengths is commonly called a "hyperspectral" sensor and would be in operation along LOS 408.

Returning to FIG. 4A, the detected intensity value I, for example of LOS 408, corresponds to a summation of the emissions from all the ions along LOS 408 from detecting vehicle 402 to lower boundary 210 of ionosphere 208. The detected intensity value I and the geometry (direction of the vector) of LOS 408 are passed to calculating portion 606 via detected signal 624.

Returning to FIG. 7, once the scan is complete, it is determined whether the most recent scan is the last scan to be performed (S710). Continuing with the example discussed above, and returning to FIG. 4A, presume that LOS 410 is to be scanned next. With reference to FIG. 6, control signal 618 from controlling portion 602 had instructed detector 604 of the scanning fan, which includes the number and placement of LOSs. Accordingly, at this point, detector 604 would know that LOS 410 is to be scanned after LOS 408.

In this example, since LOS 408 is not the last scan to be performed, it then scans LOS 410 (S708). For example, as shown in FIG. 4A, detecting vehicle detects an intensity value from LOS 410. This may be accomplished, as shown in FIG. 6, by detecting portion 612. Detector 604 knows where to start its scanning fan as instructed by controlling portion 602 via control signal 618. Accordingly, detecting portion 612 is directed to detect an intensity value along LOS 410. Detecting portion 612 may be any known type of intensity detector, a non-limiting example of which includes a photodiode. As mentioned previously, in some embodiments, detecting portion 612 may be a hyperspectral detector, operable to detect an intensity values corresponding to a plurality of distinct wavelengths, along LOS 410.

Returning to FIG. 4A, the detected intensity value I, for example of LOS 410, corresponds to a summation of the emissions from all the ions along LOS 410 from detecting vehicle 402 to lower boundary 210 of ionosphere 208. The detected intensity value I and the geometry (direction of the vector) of LOS 410 are passed to calculating portion 606 via detected signal 624.

It should be noted that the scan of LOS 408 occurs at a first time $t_1$ whereas the scan of LOS 410 occurs at a second later time $t_2$. Accordingly, when scanning LOS 408, detecting vehicle 402 is at a first position (presuming it is moving at a velocity), whereas when scanning LOS 410, detecting vehicle 402 is at a second position. For purposes of discussion simplification, presume that the rate of scanning is much larger than the velocity of detecting vehicle 402. In such a case, when scanning the fan that includes LOS 408, LOS 410, LOS 412, LOS 414 and LOS 416, presume that detecting vehicle 402 (and therefore detector 604) is at the same location.

The process of scanning (S708) and determining whether the most recent scan is the last scan (S710) continues throughout a scanning fan. For example, after the scanning of LOS 408, LOS 410, LOS 412, LOS 414 and LOS 416 of FIG. 4A, detector 604 will scan LOS 418, LOS 420, LOS 422, LOS 424 and LOS 426 of FIG. 4B. In particular, detector 604 will know the number of scans it is to perform based on instruction from controlling portion 602. In the example illustrated in FIG. 5, detector 604 scans a plurality of fans, with a sample shown as fan 502 and fan 504. In the example of FIG. 5, the scanning is complete, when a sufficient number of fans are scanned to obtain data points for grid 510.

In the present example embodiment, detector 604 includes four detecting portions, each scanning a LOS in turn. Of course in other embodiments, detector 604 may include additional detecting portions, one for each predetermined scanned LOS. In still other embodiments, a single detecting portion is used to scan all LOSs.

Returning to FIG. 7, once it is determined that the scanning is complete, then the ion altitude function for the entire scan plane is calculated (S712).

In simple terms, the observed intensity [y], is related to the geometric factor [a] and the ion altitude function [v] as follows:

$$[y]=[a][x];$$

where [y] is a vector of the observed intensity values [$y_0$, $y_1$, ..., $y_{n-1}$, $y_n$], e.g., the intensity values measured from LOS 408-426 of FIGS. 4A-B, where [a] is the corresponding tensor (a two dimensional matrix) of the geometries of the LOSs as they pass through each cell in the retrieval grid [$a_{00}$, $a_{10}$, ..., $a_{n-1,n}$, $a_{nn}$], e.g., the corresponding directions of LOSs 408-426 of FIGS. 4A-4B, and [x] is the corresponding vector of emission rates [$x_0$, $x_1$, ..., $x_{n-1}$, $x_n$].

Since [y] is measured and since [a] is known, for example, as instructed from controlling portion 602, then [v] may be determined conceptually as follows by determining the "inverse" of the geometries of the LOSs:

$$[a]^{-1}[y]=[x]$$

The above description for determining [x] is purely a conceptual one: prior art defines many techniques for solving a general class of problems known as inverse problems by a technique known as tomographic inversion. Inverse problems are referred to as such because one seeks the distribution of a parameter that creates, by emission and/or absorption the feature or features detected. Tomographic reconstruction of the ionosphere from UV brightness measurements requires inversion of a discrete forward model that relates the observed brightness values to ionospheric electron density. The brightness value recorded by the instrument within detecting vehicle 402 is proportional to the square of the electron density integrated along the instrument's LOS. The line integral can be discretized by dividing the two-dimensional ionosphere into a series of basis functions that are non-zero over a cell, e.g., a 10 km by 10 km cell, of the ionosphere. The electron density value is considered constant within individual cells. A LOS measurement $y_i$ is then related to the squared electron density values $x_j$ by the following equation:

$$y_i = \sum_j a_{ij} x_j,$$

where $a_{ij}$ is proportional to the length of the LOS i in cell j. A series of LOS measurements can then be related to ionospheric electron density by the matrix equation:

$$y=Ax,$$

where y is a vector of LOS measurements, x is a vector of squared electron densities, and A is a projection matrix determined from a geometrical forward model of LOSs from detecting vehicle 402.

The inverse problem can be solved by any known technique. For the purposes of illustration, assume that the individual contribution from each of the idealized cells is determined by determining the solution set that minimizes the cost function:

$$J(x)=\|y-Ax\|^2+\lambda\phi(Dx)$$

For illustrative purposes, the minimization problem may be solved using a conjugate gradient approach. The two terms in the cost function are a least-squares term which enforces data fidelity and a regularization function that ensures a smooth ionosphere and reduces the impact of noise on the solution. The regularization function includes a weighted gradient term $\phi(Dx)$ that preserves edges in the image. The regularization parameter) balances data fidelity and smoothness in the reconstruction.

Returning to FIG. 7, once the ion altitude function is calculated, the result is output (S714). For example, the ion altitude function may be provided as an image on a screen or provided to a transmitter for further processing. Returning to FIG. 5, the output may be grid 510, wherein a graphical user interface enables a user to select any one column. In this example, let the column selected be that corresponding to dotted line 516. Accordingly, the user may be provided with the ion altitude function of the column of ionosphere 208 corresponding to the location of dotted line 516.

A system, for example one including a passive ultraviolet sensor, and its associated concept of operations in accordance with aspects of the present invention can recover the spatial structure of an inhomogeneous radiating layer when immersed within the medium. This design enables the recovery of the two dimensional structure of the upper atmosphere without requiring that the instrument rotate or be above the medium.

Aspects of the present invention are novel in that they address the problem of making these measurements from a vehicle that is immersed with the atmosphere. For ionospheric observations, that means an altitude from about 300 km through about 500 km. It will be noted, however, that additional aspects of the present invention may be applied to any medium and that the atmosphere, and the ionosphere in particular, are merely non-limiting examples used for purposes of discussion.

The foregoing description of various embodiments of the invention have been presented for purposes of illustration and description. It is not intended to be exhaustive or to limit the invention to the precise forms disclosed, and many modifications and variations are possible in light of the above teaching without departing from the spirit or scope of the present invention. The example embodiments, as described herein, were chosen and described to best explain the principles of the invention and its practical application to thereby enable others skilled in the art to best utilize the invention in various embodiments and with various modifications as are suited to the particular use contemplated. The scope of the invention is defined by the claims appended hereto.

What is claimed is:

1. A system for measuring a parameter of a medium with a vehicle moving in a traveling direction through the medium, said system comprising:
   a first detecting portion which detects a first value of the parameter from a first line-of-sight in a first direction at a first position of the vehicle at a first time;
   a second detecting portion which detects a second value of the parameter from a second line-of-sight in a second direction at a second position of the vehicle at a second time;
   a third detecting portion which detects a third value of the parameter from a third line-of-sight in a third direction at a third position of the vehicle at a third time;
   a fourth detecting portion which detects a fourth value of the parameter from a fourth line-of-sight in a fourth direction at a fourth position of the vehicle at a fourth time; and
   a calculating portion which calculates the parameter based on the first value, the second value, the third value and the fourth value, wherein
   the first line-of-sight and the third line-of-sight are in a first plane and intersect at a first intersection,
   the second line-of-sight and the fourth line-of-sight are in a second plane and intersect at a second intersection, and
   the calculating portion calculates the parameter based additionally on the first intersection and the second intersection.

2. The system of claim 1, wherein
   at least a portion of the second line-of-sight is in the first plane,
   the first direction and the second direction form an obtuse angle, and
   the obtuse angle includes a maximum direction in the first plane which is beyond the zenith direction, which is perpendicular to the traveling direction, and further includes a minimum direction in the first plane which is below the traveling direction.

3. The system of claim 2, wherein said first detecting portion detects the first value of the parameter as a value of a spectral signature.

4. The system of claim 3, wherein the value of the spectral signature includes ultraviolet wavelengths.

5. The system of claim 4, wherein the value of the spectral signature includes wavelengths from about 40 nanometers through about 300 nanometers.

6. The system of claim 3, wherein said first detecting portion detects the value of the spectral signature of at least one selected from the group consisting of atomic oxygen, molecular oxygen, molecular nitrogen, nitric oxide, ozone, helium, hydrogen and singly ionized atomic oxygen.

7. A method of measuring a parameter of a medium with a vehicle moving in a traveling direction through the medium, said method comprising:
   detecting, using a first detecting portion, a first value of the parameter from a first line-of-sight in a first direction at a first position of the vehicle at a first time;
   detecting, using a second detecting portion, a second value of the parameter from a second line-of-sight in a second direction at a second position of the vehicle at a second time;
   detecting, using a third detecting portion, a third value of the parameter from a third line-of-sight in a third direction at a third position of the vehicle at a third time;
   detecting, using a fourth detecting portion, a fourth value of the parameter from a fourth line-of-sight in a fourth direction at a fourth position of the vehicle at a fourth time; and
   calculating, using a calculating portion, the parameter based on the first value, the second value, the third value and the fourth value, wherein
   the first line-of-sight and the third line-of-sight are in a first plane and intersect at a first intersection,
   the second line-of-sight and the fourth line-of-sight are in a second plane and intersect at a second intersection, and
   said calculating comprises calculating the parameter based additionally on the first intersection and the second intersection.

8. The method of claim 7, wherein
   at least a portion of the second line-of-sight is in the first plane,
   the third direction and the fourth direction form an obtuse angle, and
   the obtuse angle includes a maximum direction in the first plane which is beyond the zenith direction, which is perpendicular to the traveling direction, and further includes a minimum direction in the first plane which is below the traveling direction.

9. The method of claim 8, wherein said detecting, using the first detecting portion, comprises detecting the first value of the parameter as a value of a spectral signature.

10. The method of claim 9, wherein the value of the spectral signature includes ultraviolet wavelengths.

11. The method of claim 10, wherein the value of the spectral signature includes wavelengths from about 40 nanometers through about 300 nanometers.

12. The method of claim 9, wherein said detecting the first value of the parameter as the value of a spectral signature further comprises detecting the value of the spectral signature of at least one selected from the group consisting of atomic oxygen, molecular oxygen, molecular nitrogen, nitric oxide, ozone, helium, hydrogen and singly ionized atomic oxygen.

13. A tangible computer-readable media including computer-readable instructions stored thereon, the computer-readable instructions being capable of being read by a computer to be used for measuring a parameter of a medium with a vehicle moving in a traveling direction through the medium, the tangible computer-readable instructions being capable of instructing the computer to perform a method comprising:
   detecting, using a first detecting portion, a first value of the parameter from a first line-of-sight in a first direction at a first position of the vehicle at a first time;
   detecting, using a second detecting portion, a second value of the parameter from a second line-of-sight in a second direction at a second position of the vehicle at a second time;
   detecting, using a third detecting portion, a third value of the parameter from a third line-of-sight in a third direction at a third position of the vehicle at a third time;
   detecting, using a fourth detecting portion, a fourth value of the parameter from a fourth line-of-sight in a fourth direction at a fourth position of the vehicle at a fourth time; and
   calculating, using a calculating portion, the parameter based on the first value, the second value, the third value and the fourth value, wherein
   the first line-of-sight and the third line-of-sight are in a first plane and intersect at a first intersection,
   the second line-of-sight and the fourth line-of-sight are in a second plane and intersect at a second intersection, and said calculating comprises calculating the parameter based additionally on the first intersection and the second intersection.

14. The tangible computer-readable media of claim 13, wherein
at least a portion of the second line-of-sight is in the first plane,
the third direction from the vehicle and the fourth direction from the vehicle form an obtuse angle, and
the obtuse angle includes a maximum direction in the first plane which is beyond the zenith direction, which is perpendicular to the traveling direction, and further includes a minimum direction in the first plane which is below the traveling direction.

15. The tangible computer-readable media of claim 14, wherein said detecting, using the first detecting portion, comprises detecting the first value of the parameter as a value of a spectral signature.

16. The tangible computer-readable media of claim 15, wherein the value of the spectral signature includes ultraviolet wavelengths.

17. The tangible computer-readable media of claim 16, wherein the value of the spectral signature includes wavelengths from about 40 nanometers through about 300 nanometers.

18. The tangible computer-readable media of claim 15, wherein said detecting the first value of the parameter as the value of the spectral signature comprises detecting the value of the spectral signature of at least one selected from the group consisting of atomic oxygen, molecular oxygen, molecular nitrogen, nitric oxide, ozone, helium, hydrogen and singly ionized atomic oxygen.

* * * * *